United States Patent [19]

Koch et al.

[11] 4,252,980

[45] Feb. 24, 1981

[54] PROCESS FOR THE MANUFACTURE OF (PHENOXY OR BENZYL)-PHENOXYPROPIONIC ACID METHYL ESTERS

[75] Inventors: Manfred Koch, Eppstein; Hilmar Mildenberger, Kelkheim, both of Fed. Rep. of Germany

[73] Assignee: Hoechst Aktiengesellschaft, Frankfurt an Main, Fed. Rep. of Germany

[21] Appl. No.: 81,052

[22] Filed: Oct. 2, 1979

[30] Foreign Application Priority Data

Oct. 4, 1978 [DE] Fed. Rep. of Germany ....... 2843184

[51] Int. Cl.³ .............................................. C07C 79/46
[52] U.S. Cl. ........................................ 560/21; 560/57; 560/61; 560/62
[58] Field of Search ................. 560/21, 62, 57, 61

[56] References Cited

U.S. PATENT DOCUMENTS

| 3,334,125 | 8/1967 | Richter ................................. 560/62 |
| 4,088,474 | 5/1978 | Matterstock et al. ................. 560/21 |
| 4,106,925 | 8/1978 | Rohr et al. ............................ 560/21 |

OTHER PUBLICATIONS

Zeinalov et al., Chem. Absts., 66, 30233(h), 1967.
Migrdichian, Organic Synthesis, Reinhold Publishing Co., vol. 1, p. 327, 1957.

*Primary Examiner*—Natalie Trousof
*Assistant Examiner*—G. T. Breitenstein
*Attorney, Agent, or Firm*—Curtis, Morris & Safford

[57] ABSTRACT

(Phenoxy- or benzyl)-phenoxypropionic acid methyl esters are produced by esterification of the corresponding anhydrous alkali metal salts with half the molar amount of dimethyl sulfate at a temperature exceeding 120° C.

2 Claims, No Drawings

PROCESS FOR THE MANUFACTURE OF (PHENOXY OR BENZYL)-PHENOXYPROPIONIC ACID METHYL ESTERS

This invention relates to a process for the manufacture of (phenoxy or benzyl)-phenoxypropionic acid methyl esters of the formula

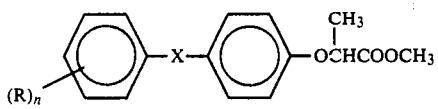

in which the radicals R, which are identical or different, are alkyl, halogen, $CF_3$ or $NO_2$, n is 1 or 2 and X is oxygen or the group —$CH_2$—, which comprises reacting anhydrous alkali metal salts of correspondingly substituted (phenoxy or benzyl)-phenoxypropionic acids with an approximately semi-molar amount of dimethyl sulfate in an inert non-polar solvent at a temperature above 120° C.

The compounds of the formula I are highly effective and selective grass herbicides which are known from German Offenlegungsschrift Nos. 2,223,894, 2,417,487, 2,433,067, 2,601,548 and 2,652,584.

The alkylation of carboxylic acid salts with dimethyl sulfate to give carboxylic acid methyl esters is known. In general, the dimethyl sulfate is used in an equimolar amount or in an excess calculated on the carboxylic acid salt (cf. Houben-Weyl, volume VIII, page 542 (1952); Ullmann, 4th edition, volume 10, page 103 (1975); Monatshefte für Chemie 99, page 103 (1968); C.A. 49, 11594 h (1953)). The yields of 82 to 96% of the theory obtained are, however, unsatisfactory for industrial purposes. Moreover, the above process has the disadvantage that one half of the dimethyl sulfate is lost in the form of methylsulfuric acid. In addition, residues of unreacted dimethyl sulfate always remain which, because of the danger of ester hydrolysis, cannot be removed by means of alkali metal hydroxide solution after termination of the reaction as it is done, for example, in the phenol etherification with dialkyl sulfates. Because of the toxicity of dimethyl sulfate, this method is, therefore, unsuitable especially for the manufacture of compounds for biological uses.

Attempts have been made to utilize the methylsulfuric acid salt formed in the reaction for further esterification according to the following scheme, in order to reduce the amount of dimethyl sulfate required:

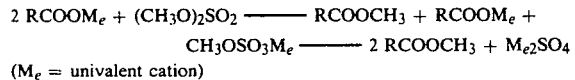

($M_e$ = univalent cation)

According to Houben-Weyl (loc.cit.) this reaction is successful only under pressure and at elevated temperature (no details are given). Ullmann (loc.cit.) states in the same connection that a prolonged after-reaction at elevated temperature is necessary. A process for the alkylation of benzoic acid salts with the semimolar amount of dimethyl sulfate described in Ann. 340, page 246 (1905) requires reaction temperatures of from 180° to 260° C. and yields only 75% of the theory of benzoic acid methyl ester. The alkylation of potassium benzoate with a molar amount of the potassium salt of methylsulfuric acid at 210° to 250° C. gives still lower yields.

The alkylation of sodium salts of fatty acids with half the molar amount of dimethyl sulfate in water, as described in C.A. 66, 30233 h (1967), takes place at a temperature of 150° C., but, although a long reaction time of at least 10 hours is required, a yield of about 85% only of fatty acid methyl ester is obtained (cf. Ullmann loc. cit.).

It is therefore surprising that with the use of the starting substances according the invention the reaction with half the molar amount of dimethyl sulfate gives the compounds of the formula I in an almost quantitative yield at substantially lower reaction temperatures and in a much shorter time.

The reaction proceeds according to the following equation

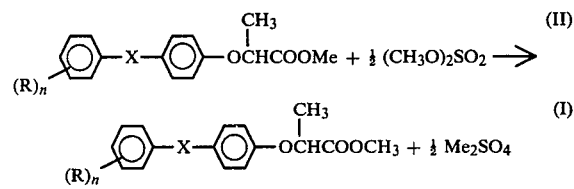

To carry out the reaction, the anhydrous alkali metal salts of the formula II are suspended in an inert, non polar solvent, preferably a hydrocarbon such as benzene, toluene, xylene or cumene, or a halohydrocarbon such as chlorobenzene and dichlorobenzene, preferably xylene, and dimethyl sulfate is added to the suspension.

The reaction of dimethyl sulfate to the methylsulfuric acid salt takes place spontaneously and is sufficiently rapid even at low reaction temperatures, whereas a reaction temperature of at least 120° C. is required for converting the methyl-sulfuric acid salt to sodium sulfate. With solvents or diluents having a lower boiling point the boiling temperature must be raised by application of external pressure. The reaction time required for a quantitative conversion of salts of the formula II depends on the reaction temperature; it is approximately 1 hour for a reaction temperature of 135° C. When the reaction is complete, the reaction mixture has a neutral reaction. Inorganic salts can be removed directly or after acidification with a small amount of mineral acid either by washing with water or by filtration or centrifugation.

With the use of a semimolar amount of dimethyl sulfate (calculated on the salt used) a conversion of 99.3 to 99.5% of the theory is obtained. If the dimethyl sulfate is used in a minor excess (5%), calculated on the semimolar amount of the salt of formula II used, a conversion of over 99.8% is reached. To obtain optimum results an excess of up to 10% can be used.

The following examples illustrate the invention.

EXAMPLE 1

Methyl-2-[4'-(4''-trifluoromethylphenoxy)-phenoxy]-propionate 63 g of dimethyl sulfate are added within 5 minutes and at 130° C. to 348 g of anhydrous sodium-2-[4'-(4''-trifluoromethyl-phenoxy)-phenoxy]-propionate, suspended in 1,000 ml of xylene. After the addition, stirring of the mixture is continued for 1 hour, the mixture is cooled at 85° C., at said temperature 200 ml of water and 0.5 ml of $H_3PO_4$ are added and, for the separation of the inorganic salts, the mixture is stirred for 10 minutes. After separation of the water phase, the xylene is distilled off. 340 g of methyl-2-[4'-(4''-trifluoromethylphenoxy)-phenoxy]-propionate are obtained melting at 142° C. under 0.05 torr. According to gas chromatogram the content of pure final product is 99.4%, the residual content of unreacted acid is 0.6%, which corresponds to a yield of 99.4%.

EXAMPLE 2

Methyl-2-[4'-(2'',4''-dichlorophenoxy)-phenoxy]propionate 66.2 g of dimethyl sulfate are added within 5 minutes and at 130° C. of 349 g of anhydrous sodium-2-[4'-(2'',4''-dichlorophenoxy)-phenoxy]-propionate in 1,000 ml of xylene. After the addition, the reaction mixture is stirred for 1 hour at 138° C., whereupon it is cooled to 90° C. Next, 200 ml of water are added to the reaction mixture.

The mixture is intensely stirred for 10 minutes at 85° C., the water phase is separated and the xylene is distilled of. 341 g of methyl-2-[4'-(2'',4''-dichlorophenoxy)-phenoxy]-propionate melting at 168° C. under 0.05 torr are obtained. According to gas chromatogram the content of pure final product is 99.9%, which corresponds to a yield of 99.9%.

The following compounds are obtained in analogous manner and with the same yield:
methyl-2-[4'-(4''-chlorophenoxy)-phenoxy]-propionate
melting point 154° C. under 0.15 torr;
methyl-2-[4'-(4''-chlorobenzyl)-phenoxy]-propionate
melting point 144° to 148° C. under 0.07 torr;
methyl-2-[4'-(2'',4''-dichlorobenzyl)-phenoxy]-propionate melting point 158° to 161° C. under 0.05 torr;
methyl-2-[4'-(2''-chloro-4''-trifluoromethylphenoxy)-phenoxy]-propionate, melting point 155° C. under 0.05 torr;
methyl-2-[4'-(4''-bromo-2''-chlorophenoxy)-phenoxy]-propionate melting at 195° to 198° C. under 0.4 torr;
methyl-2-[4'-(4''-chloro-2''-nitrophenoxy)-phenoxy]-propionate melting point 224° to 300° C. under 3 torr.

What is claimed is:

1. In a process for the manufacture of (phenoxy or benzyl)-phenoxypropionate acid methyl esters of the formula

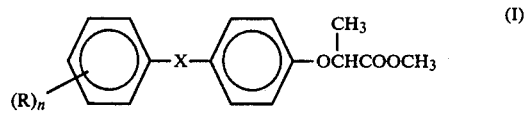

in which the radicals R, which are identical or different, are alkyl, halogen, $CF_3$ or $NO_2$, n is 1 or 2 and X denotes oxygen or the group —$CH_2$—, the improvement which comprises reacting anhydrous alkali metal salts of correspondingly substituted (phenoxy or benzyl)-phenoxypropionic acids with an approximately semimolar amount of dimethyl sulfate in an inert nonpolar hydrocarbon or halohydrocarbon solvent at a temperature above 120° C.

2. The process of claim 1, wherein the reaction is carried out at a temperature of from 120° to 150° C.

* * * * *